United States Patent [19]

Smoler

[11] Patent Number: 4,622,012
[45] Date of Patent: Nov. 11, 1986

[54] DENTAL POST SYSTEM

[76] Inventor: Lewis S. Smoler, 450 Plandome Rd., Manhasset, N.Y. 11030

[21] Appl. No.: 716,489

[22] Filed: Mar. 27, 1985

[51] Int. Cl.$^4$ ............................................. A61C 5/08
[52] U.S. Cl. .................................................. 433/221
[58] Field of Search ................ 433/218, 220, 221, 222

[56] References Cited

U.S. PATENT DOCUMENTS

| | | |
|---|---|---|
| 6,114 | 2/1849 | Clark . |
| 275,491 | 4/1883 | How . |
| 347,975 | 8/1886 | Starr . |
| 430,522 | 6/1890 | Genese . |
| 644,803 | 3/1900 | Justi . |
| 731,594 | 6/1903 | Mosley . |
| 965,246 | 7/1910 | Stallman ............................ 433/221 |
| 989,248 | 4/1911 | Gollobin et al. . |
| 1,583,459 | 4/1925 | Hansen . |
| 2,536,669 | 1/1951 | Thau-Jensen ...................... 433/221 |
| 3,629,943 | 12/1971 | Gindea . |
| 4,253,835 | 3/1981 | Ware . |
| 4,362,508 | 12/1982 | Soderstrom ......................... 433/81 |

OTHER PUBLICATIONS

Tjan, *The Effect of a Corrugated Channel on the Retentive Properties of an Obturator-Reinforced Composite Resin Dowel-Core System*, The Journal of Prosthetic Dentistry, Mar. 1984, pp. 347-351.

Dental Consultants, Inc., *Composites*, The Dental Advisor, Fall 1984, pp. 1-8.
Whaledent International, *Para-Post System Unlimited*, Jun. 1982.
Essential Dental Systems, *Flexi-Post: The Proven Low-Stress Prefab*, Copyright 1982.

*Primary Examiner*—Robert Peshock
*Attorney, Agent, or Firm*—Lee C. Robinson, Jr.

[57] ABSTRACT

The restoration of a diseased or damaged tooth is carried out by decoronating the tooth leaving the root canal exposed. Then the canal is reamed, cleaned, irrigated, and obturated. It is then rereamed to a predetermined size leaving the apical portions filled with obturatory material and treated with a dentinal bonding agent. A perforated, hollow tubular outer post is inserted into the prepared canal and a paste or liquid composite is injected into the canal through the outer post. A serrated rod-like inner post is inserted into the outer post, and distributes the composite within the canal, forcing excess into the coronal area. After insertion, a spade-shaped top end of the inner post projects from the canal. A prep former is filled with a dental composite and is emplaced on the root over the inner rod upper end. This hardens to become a crown core onto which a prosthetic crown is affixed. This technique permits one-visit treatment, precludes abnormal internal stresses to the root structure, and can be carried out on unusual, difficult canal roots using standard dental equipment.

19 Claims, 15 Drawing Figures

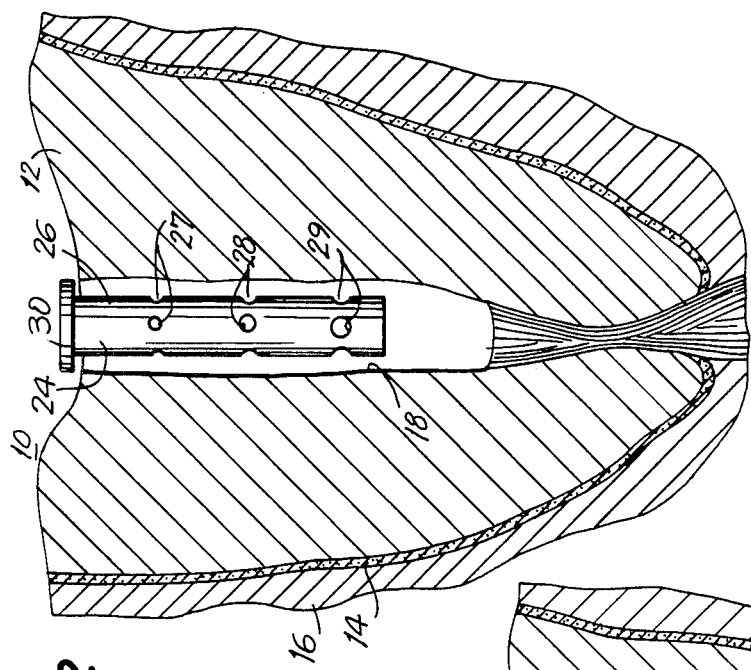
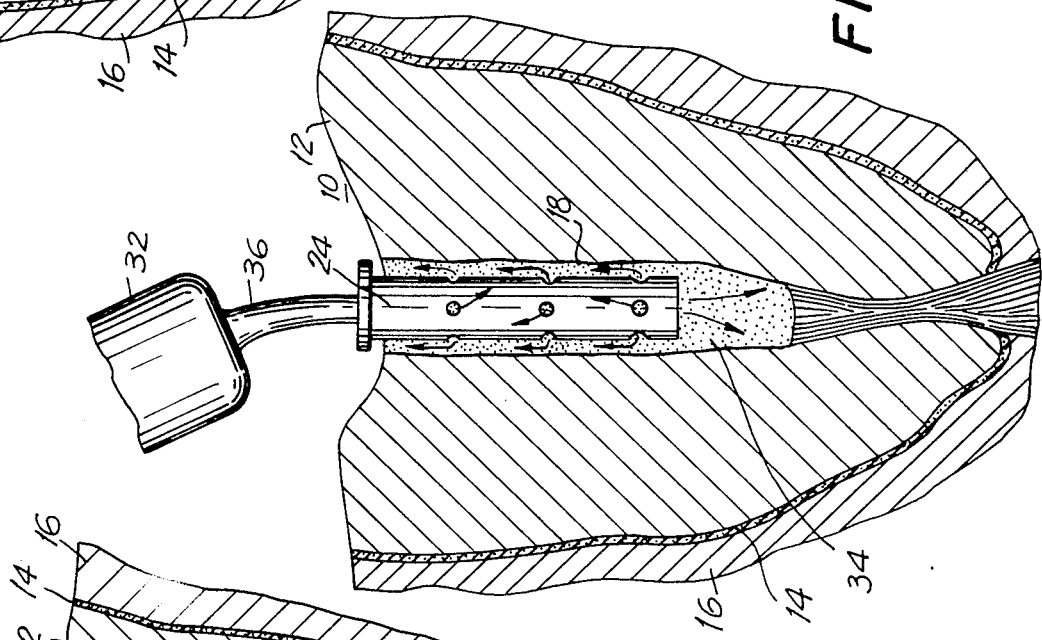
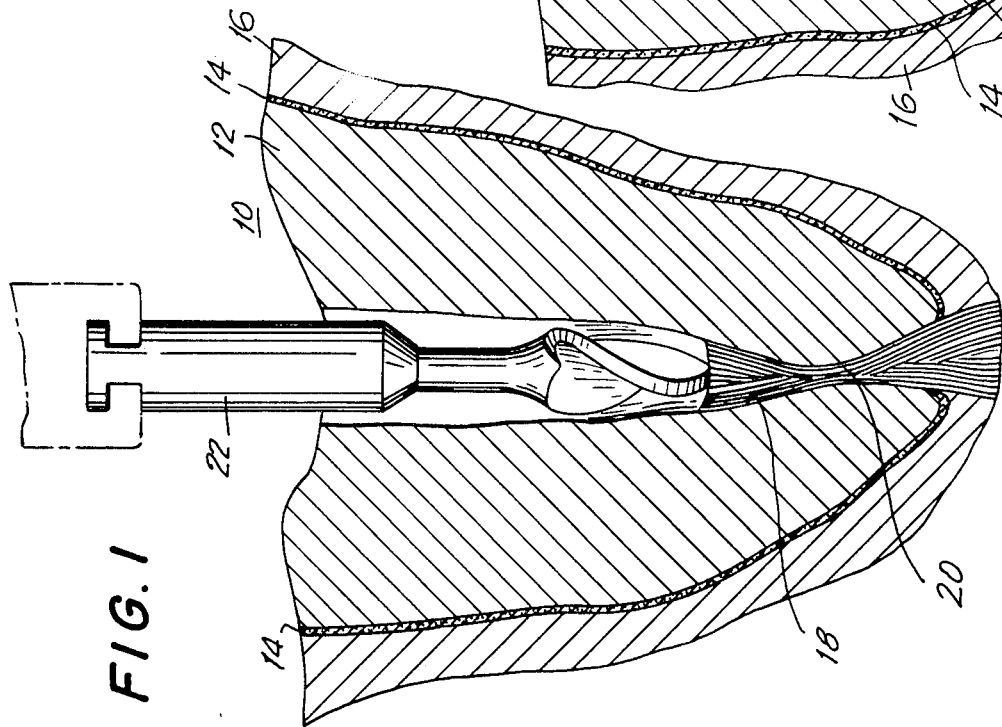

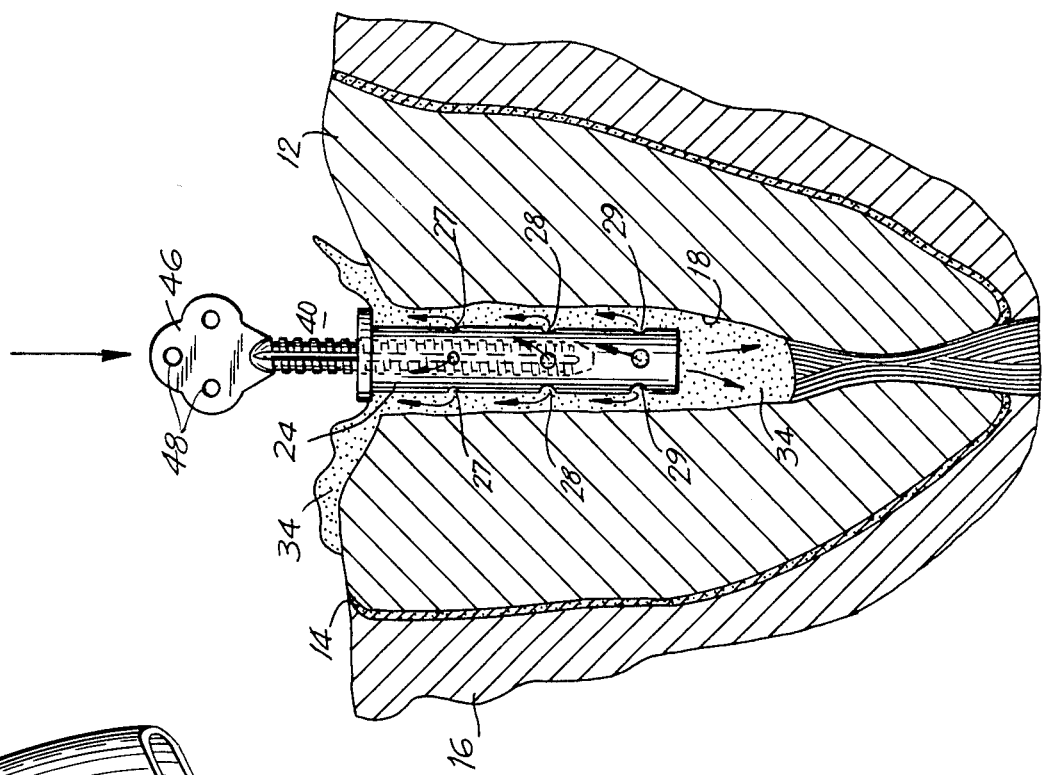
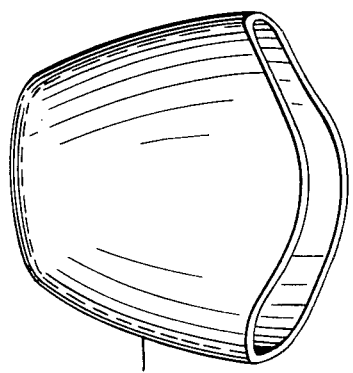
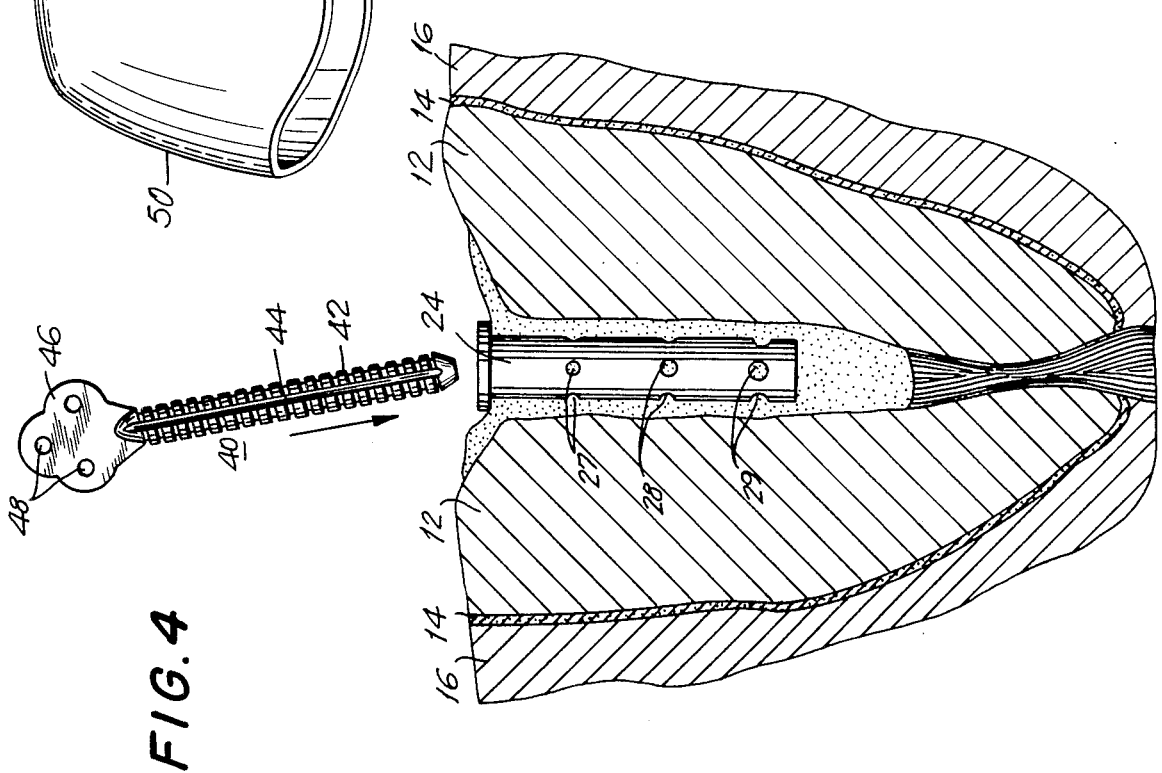

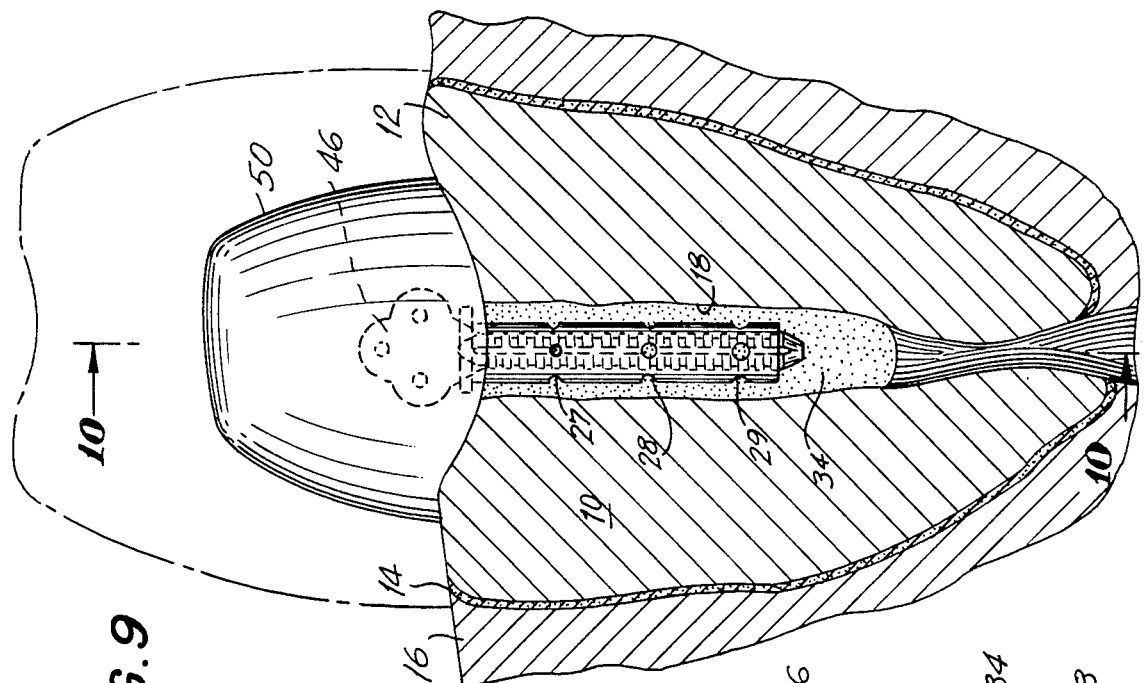
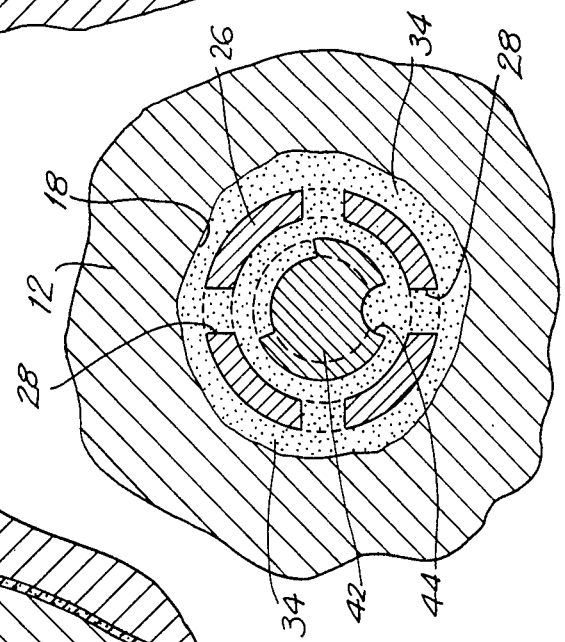
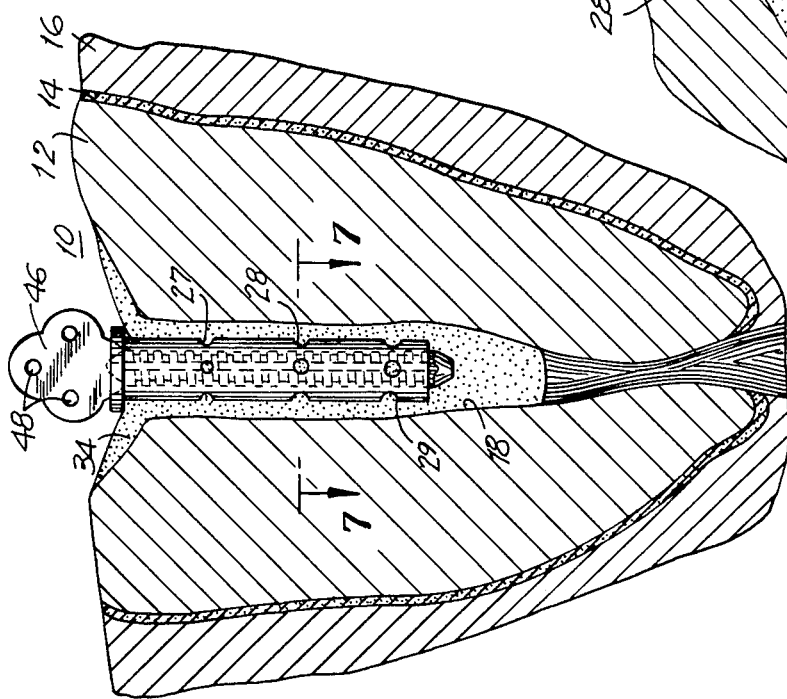

DENTAL POST SYSTEM

The present invention relates to dental prosthetics, and is more particularly directed to a two-part post assembly for securing an artificial crown to the root of a tooth which may have become diseased or broken.

Many post or dowel systems exist in the dental prosthetics art, and many versions have been employed for dental restoration by securing an artificial crown the root of the tooth. Unfortunately, these prior post or dowel systems are either difficult to use, can only be employed in special circumstances, or else run the risk of cracking the root of the tooth, and then inflicting irreparable damage to the root.

In a conventional post or dowel system, the diseased or broken tooth is decoronated (i.e., its crown is removed at the cervix) and the root canal (or each root canal in a posterior tooth) is drilled out and reamed to a proper size. Then the canal is cleaned, irrigated, and obturated. Then the coronal two-thirds of the canal is again reamed out. At that time, a stainless steel post is selected and is inserted into the prepared root canal. The restoration work, which can be an artificial crown, is then secured to the root by means of an exposed upper end of the post.

With this type of system, the stainless steel post must fit snugly into the canal. However, upon insertion or after, high stresses can crack the root. Alternatively, a tapered stainless steel post, instead of a parallel-sided post, can be employed to avoid some of the cracking stresses. Unfortunately, this requires enlargement of the canal and precision tapering at the deep end of the canal, and thus more time and care must be used.

A number of other techniques have been proposed, including, e.g., a split post system and a flexible post system, to avoid high stresses within the root. However, these proposed systems must be inserted deep in the root canal, so extreme care must be exercised in the canal preparation. Also, the split post and flexible post systems are generally of the screw-in type, and can still inflict great internal pressures on the tooth root.

A sleeve-and-rod dental restoration technique has been proposed previously, in which a tubular sleeve fits snugly within the bore of a prepared root canal for frictional engagement therewith, and a rod, on which an artificial crown or other restoration work is mounted, is inserted into the tubular sleeve. While this technique does offer some advantages, it should be recognized that the smooth surface of the rod and of the internal service of the sleeve cannot prevent rotation of the coronal restoration. Also, in this type of system the root canal must be carefully reamed to bore it out to a precise diameter.

It is an object of this invention to provide a dental restoration technique which permits a secure, one-office visit post and core preparation for restoration of a diseased or broken tooth, and which avoids the pitfalls of prior art techniques.

It is another object of this invention to provide a dental restoration technique which minimizes the risk of cracking the root from internal pressures.

It is still another object of this invention to provide a dental restoration technique in which a post assembly is installed quickly and securely, even in difficult canals.

It is yet another object of this invention to provide a dental restoration technique in which the tooth is actually strengthened and made resistant to cracking.

It is a further object of this invention to provide a tooth preparation technique which avoids the requirement for special tools, and which can be carried out using only standard burs, dental reamers, and other standard dental equipment.

It is still another object of this invention to provide a dental restoration technique permitting economies of inventory avoiding the need to keep a large and expensive array of restoration posts on hand.

According to an object of this invention, the restoration of a damaged or diseased tooth is carried out by removing the crown and exposing the root canal, either above, at, or below the gingival margin; preparing the canal suitably for insertion of a post assembly; positioning in the prepared canal an outer post-tube, the latter being formed of a perforated, open-end, generally cylindrical hollow body; injecting a hardenable composite paste material into the canal through the outer post-tube (i.e., using the latter as a nozzle for this injection); inserting into the outer post-tube an inner post having a serrated post portion and a spade or head portion at a proximal end of the post portion, the inserting of the inner post serving to force the composite paste material through the perforations in the hollow body outer post to fill the space between the canal and the outer post, with the head portion being left exposed above the tooth root; and then attaching an artificial crown over the head portion of the inner post atop the root. This last step is favorably carried out by filling a core preform with a hardenable composite material and placing the same on the tooth root over the head portion of the inner post to form a core. After the hardenable composite material has cured, the artificial crown can be attached by cementing the same over the crown core.

According to another aspect of this invention, a kit is provided for dental restoration of damaged or diseased teeth. The kit includes at least one, and preferably an assortment of hollow, open-ended, perforated, generally cylindrical outer post bodies of a suitable dimension to be inserted into the prepared root canal of the root of the tooth to be restored, and at least one, but preferably an assortment of serrated post portions each being at least slightly longer than the respective outer post body, and insertable within the latter, and also having a broadened, spade-like head portion at a proximal end of the post portion. The kit can also include at least one hollow core prep former dimensioned to overfit the head portion of the inner post on the root when the inner post is inserted into the outer post body in the root canal of the tooth. The kit can optionally include suitable hardenable paste composite material to be injected through the outer post body into the root canal and a suitable hardenable composite material to be molded in the prep former to form a crown core anchored by the head portion of the inner post to the tooth root, and on which an artificial crown is to be secured.

The above and many other objects, features, and advantages of this invention will be more fully understood from the ensuing detailed description of a preferred embodiment, when considered in connection with the accompanying drawings in which FIGS. 1-6 are cross sectional elevational views of a tooth root at different successive stages in a dental restoration technique according to one embodiment of this invention;

FIG. 7 is a cross-sectional view taken along the line 7—7 in FIG. 6;

FIG. 8 is a perspective view of a crown core preform employed in this embodiment of the invention;

FIGS. 9 and 10 illustrate remaining steps of the restoration process according to the embodiment of this invention.

Figure 11:
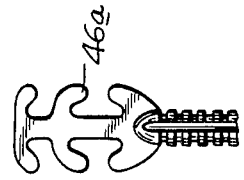
FIGS. 11-15 illustrate various alternative embodiments of spade or head-end portions of posts that can be employed with embodiments of this invention.
Figure 15:
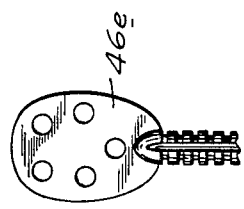
Figure 14:
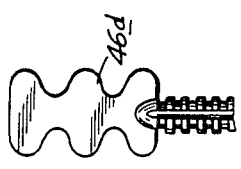
Figure 13:
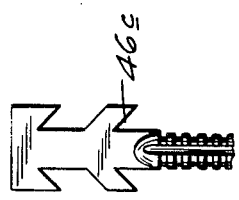
Figure 12:
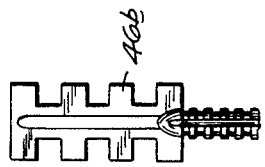

With reference to the drawings, and initially to FIG. 1 thereof, a dental restoration technique according to one embodiment of this invention is shown being carried out on a decoronated tooth root 10. The root 10 is basically composed of dentin 12 held by a cementum and periodontal ligament layer 14 to the gum or gingival tissue 16 of a patient's jaw. A root canal 18 contains the pulp 20 of the tooth.

In the step illustrated in FIG. 1, the root canal 18 is cleaned, obturated, and contoured, using standard dental instruments, in this case a Peeso reamer 22. Because of the nature of the post assembly, undercuts and/or irregular edges in the wall of the reamed-out canal 18 are preferable, as they will aid retention and prevent rotation of the post assembly. Thus, it is unnecessary for the practicioner produce a smooth circular wall on the prepared canal 18.

As shown in FIG. 2, when the canal 18 has been suitably prepared, a hollow body outer post 24 is inserted into the canal to check the fit. There should be adequate space around the post so that a composite material employed in this technique can flow in the annular space between the outer post 24 and the wall of the canal 18 without creating hydraulic stresses.

In this embodiment, the hollow body outer post 24 is formed of a generally cylindrical tubular wall 26 open at its top and bottom. There are a plurality of apertures 27, 28, and 29 along the cylindrical wall 26 near the top, middle, and bottom, respectively, of the outer post 24. In this outer post 24, the apertures 27-29 may be progressively larger from the top or proximal end to the bottom or distal end, that is, the apertures 27 are smaller than the apertures 28, which, in turn, are smaller than the apertures 29.

In this embodiment a rim or radial flange is provided at the top end of the hollow body outer post 24. But it may also be flangeless being cut from a longer length of post tube.

At this point, the canal is acid-etched, cleaned, irrigated, and dried. Then, if desired, a dentinal bonding agent can be applied to the canal.

As shown in FIG. 3, a syringe 32 containing a paste composite material 34 has a nipple 36 which fits into the top end of the hollow body outer post 24. The latter is inserted in place into the prepared root canal 18, and the composite material 34 is injected, through the outer post 24 into the root canal 18.

Because the lower or more distal apertures 29 are progressively larger than the upper apertures 27, the composite material will flow from the bottom of the apex of the canal root 18 to the top or coronal area of the tooth root 10. This feature virtually eliminates the possibility of creating air pockets or voids in the material 34.

Then, as shown in FIGS. 4 and 5, an inner post or dowel 40 is inserted into the interior of the outer post 24. This inner post 40 has a shaft or post portion 42 which is generally parallel-sided (as opposed to tapered). The post portion 42 is serrated with cuts generally across the length direction thereof, and has an axial slot or cutout 44 serving as a vent. The post portion 42 is dimensioned slightly smaller in diameter than the inner diameter of the outer post 24 and is slightly longer than the latter.

As is also shown in FIGS. 4 and 5, the inner post 40 has a flattened or spade head 46 at its upper or proximal end. In this embodiment, the head 46 is key shaped. The head 46 also has a plurality of cutouts 48 extending through it.

When the inner post 40 is inserted into the outer post 24, as shown in FIG. 5, the composite material 34 is forced outward through the bottom of the tubular wall 26, and also through the apertures 27, 28, and 29, where it flows upward in the annular space between the wall of the canal 18 and the outer surface of the tubular wall 26. There is a sufficient amount of this composite 34 so that some of it will flow outward to the coronal area, as shown in FIG. 5, where it can be cleaned away. At the end of the insertion, as shown in FIG. 6, the head 46 rests against the top of the outer post 24 and projects into the coronal area above the root 10.

As shown in FIG. 7, the composite material fills all of the space within the canal 18 that is not occupied by the cylindrical wall 26 of the outer post 24 or by the post portion 42 of the inner post 40. Irregularities and undercuts in the canal 18 are locked by the solidified composite material 34 to the serrations and the vent 44 of the post portion 42 to ensure that the head 46 of the inner post 40 will not rotate with respect to the tooth root 10.

A hollow plastic core prep former 50 (FIG. 8) is provided for molding a composite crown core over the head portion 46 atop the root 10.

Figure 10:
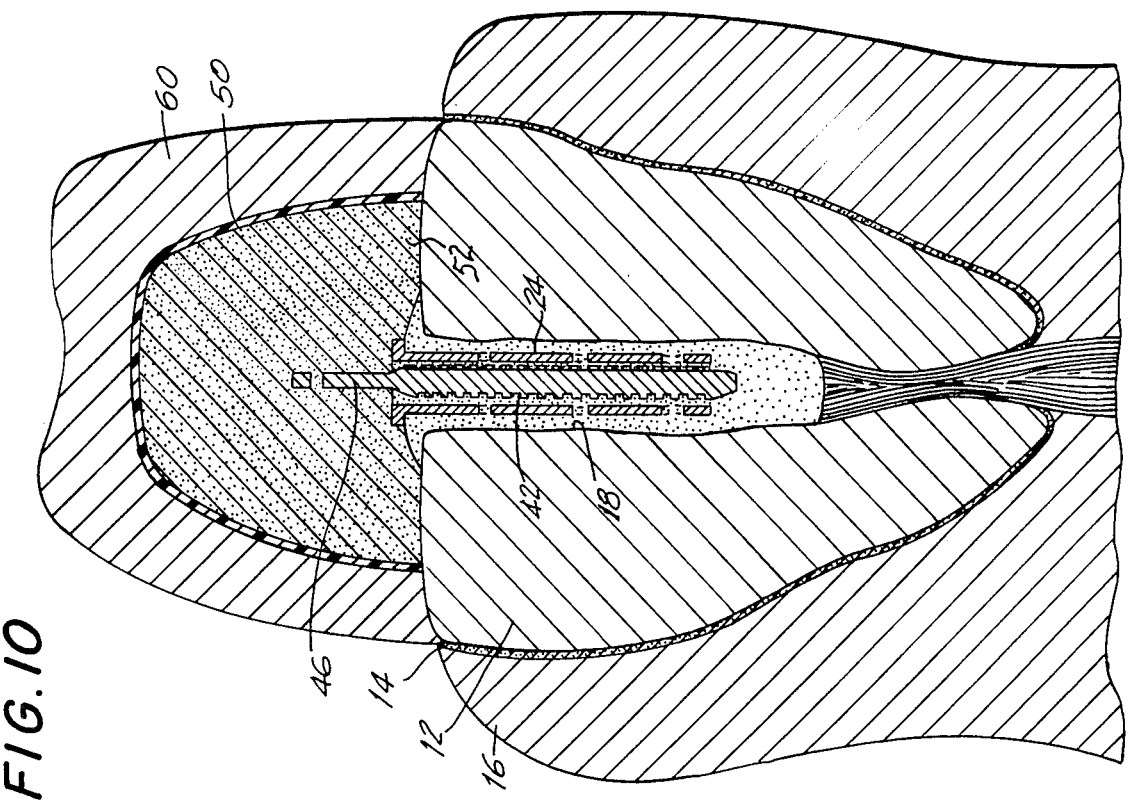

At this stage in the procedures, the prep former 50 is filled with a composite material and is positioned over the inner post head 46 in the coronal area atop the tooth root 10, as shown in FIG. 9. The composite material is permitted to harden, and, within several minutes, there is a molded post and core structure, upon which an artificial crown 60 (FIG. 10) can be affixed. In one alternative procedure, the prep former 50 remains on the crown core 52, and the artificial crown 60 is affixed directly atop the permanent core former 50. In other alternative embodiments, the core former 50 can be removed, and the crown 60 cemented directly atop the composite core 52.

It should be observed that the key-shaped head 46 of the inner post provides an excellent matrix for the composite core 52. This occurs because the composite material for the core 52 permeates the apertures or cutouts 48 and conforms with the curves and irregularities of the head 46 so that the core 52 is firmly anchored to the tooth root 10 by means of the inner post 40.

FIGS. 11 through 15 show many possible variations of the head 46a through 46e, respectively, which may be optionally employed depending on the requirements of the tooth restoration in question. In all cases, the head 46a through 46e is somewhat flattened, or spade-shaped, with cutouts provided therein to secure a good anchorage for the crown core 52.

In order to facilitate use by the dental practitioner, a kit is provided comprising an assortment of outer posts 24 in various sizes and an assortment of inner posts 40, also in various sizes, and, optionally, with an assortment of head shapes 46 and 46a-46e. In a preferred assortment, the outer posts 24 are provided in 9, 11, and 13 millimeter lengths, while the inner posts 40 are provided in 12, 14, and 16 millimeter lengths. While the Peeso reamer 22 is considered standard dental equipment, one or more such reamers 22 can also be included in the kit. The kit also includes an assortment of crown prep formers 50. In a preferred version of the kit, the composite material is provided, as are one or more syringes 32 for applying the same. Instead of individual outer post tubes of different lengths, they may be cut to size from one long length provided in different diameters.

Several advantages of this invention become quite apparent from the foregoing. Because of the unique nature of the two-part post assembly 24, 40, the presence of undercuts and/or irregular edges in the prepared canal 18 are preferable, and will aid retention and prevent rotation of the post assembly 24, 40. Also, due to the unique construction of the post assembly, it is unnecessary for either the outer post 24 or the inner post 40 to exceed two-thirds the length of the root canal 18. Therefore, this post system provides the flexibility to accommodate tapered and/or twisted canals 18, without the necessity for over preparation. This is an advantage because over preparation can weaken the remaining tooth structure.

Also, because of the use of combined solid post portions 24 and 40 and a hardenable paste or liquid composite material 34, the insertion forces of the post assembly 24, 40 results in even distribution of stresses over the entire canal 18, and prevents build-up of internal stresses, which otherwise could crack the remaining tooth root 10, and which do often so crack the tooth if other systems are employed.

Also, using the technique of this invention, the requirements for outside laboratory services and expensive materials are avoided, and there is minimal destruction of the existing matural tooth structure.

The post assembly 24, 40 is actually extruded into the prepared canal 18 and is bonded to the walls of the canal so that the hollow metal outer post 24 combines with the composite material 34 and the inner post 40 to reenforce the tooth's own strength. The techniques and materials involved provide a fast preparation and set, so that the root preparation and crown core formation can be accomplished in a single office visit. A temporary crown can be attached to the crown core, if desired, at the end of a single office visit, or if the practicioner has the resources at hand, the permanent crown 60 can be prepared on the spot and attached. The technique of this invention can even be employed to extrude teeth which are fractured below the gingival margin, or even below the crest of surrounding bone.

The technique of this invention can also be employed where it required to extrude a root which cannot otherwise be reached, without the necessity to cut away any of the gum tissue and bone. By applying on the dentin faces to the hooked post design.

The terms "top" and "bottom" are used in this description for convenience's sake, to mean the proximal end (i.e., towards the crown of the tooth) and the distal end (i.e., towards the gum or jaw). A lower tooth is shown here. However, in an upper tooth, the technique would be the same, but inverted.

The combined composite and metal post and core structure of this invention is economical to use, and requires only a very small inventory of sizes for any type of tooth restoration.

It should also be recognized that this technique can be applied in many other instances in the dental or medical practices, or outside them, where a post or other element in the nature of a rivet is to be secured to an apertured member.

While the present invention has been discussed with reference to a preferred embodiment, it should be recognized that many modifications and variations thereof would present themselves to those of skill in the art without departure from the scope and spirit of this invention, as defined in the appended claims.

What is claimed is:

1. A method of restoring a damaged or diseased tooth having a tooth root with a root canal, from which a tooth crown has been removed exposing said canal, comprising
   preparing said canal suitably for insertion of a post;
   loosely positioning in the prepared canal an outer post to form a space between said outer post and said canal, the outer post being formed of a perforated, open-ended generally cylindrical hollow body;
   injecting a hardenable composite material into the canal through said outer post;
   inserting into the outer post an inner post having a serrated post portion and a head portion at a proximal end of the post portion, the inserting including forcing said composite material through perforations in said hollow body outer post to fill the space between said canal and said outer post, said head portion being exposed above the tooth root; and
   attaching an artificial crown over said head portion of said inner post atop said root.

2. A method of restoring a damaged or diseased tooth having a tooth root with a root canal, from which a tooth crown has been removed exposing said canal, comprising
   preparing said canal suitably for insertion of a post;
   applying a dentin bonding agent to the prepared canal;
   loosely positioning in the prepared canal an outer post to form a space between said outer post and said canal, the outer post being formed of a perforated, open-ended generally cylindrical hollow body;
   injecting a hardenable composite material into the canal through said outer post;
   inserting into the outer post an inner post having a serrated post portion and a head portion at a proximal end of the post portion, the inserting including forcing said composite material through perforations in said hollow body outer post to fill the space between said canal and said outer post, said head portion being exposed above the tooth root; and
   attaching an artificial crown over the head portion of said inner post.

3. A method of restoring a damaged or diseased tooth having a tooth root with a root canal, from which a tooth crown has been removed exposing said canal,
   preparing said canal suitably for insertion of a post;
   loosely positioning in the prepared canal an outer post, to form a space between said outer post and said canal the outer-post being formed of a perforated, open-ended generally cylindrical hollow body, said body having apertures of progressively larger size from an upper to a lower end thereof;
   injecting a hardenable composite material into the canal through said outer post;
   loosely inserting into the outer post an inner post having a serrated post portion and a head portion at a proximal end of the post portion, the inserting including forcing said composite material through perforations in said hollow body outer post to fill the space between said canal and said outer post, said head portion being exposed above the tooth root; and attaching an artificial crown over the head portion of said inner post.

4. The method of claim 3, wherein said outer post has a radial flange at its upper end.

5. A method of restoring a damaged or diseased tooth having a tooth root with a root canal, from which a tooth crown has been removed exposing said canal, comprising reaming out said canal with a reamin device;

preparing the reamed-out canal for insertion of a post assembly;

loosely positioning in the prepared, reamed-out canal an outer post to form a space between said outer post and said canal, the outer post being formed of a perforated, open-ended generally cylindrical hollow body;

injecting a hardenable composite material into the canal through said outer post;

inserting into the outer post an inner post having a generally parallel-sided post portion and a head portion at a proximal end of the post portion, said post portion having a vent cut-out extending along its length, and serrations cutting generally across its length the inserting including forcing said composite material through perforations in said hollow body outer post to fill the space between said canal and said outer post, said head portion being exposed above the tooth root the inner and outer posts together forming the post assembly; and attaching an artificial crown over the head portion of said inner post.

6. The method of claim 5, wherein said reaming includes contouring the canal to leave irregularities in the side wall of the reamed-out canal to aid retention and prevent rotation of the post assembly.

7. A method of restoring a damaged or diseased tooth having a tooth root with a root canal, comprising decornating said tooth at a cervix thereof to expose said canal;

reaming out said canal with a reaming device;

preparing said canal suitably for insertion of a post;

loosely positioning in the reamed-out, prepared canal an outer post to form a space between said outer post and said canal, the outer post being formed of a peforated, open-ended generally cylindrical hollow body;

injecting a hardenable composite paste material into the canal through said outer post;

inserting into the outer post an inner post having a serrated post portion and a head portion at a proximal end of the post portion, the insertion including forcing said composite paste material through perforations in said hollow body outer post to fill the space between said canal and said outer post, said head portion being exposed above the tooth root;

forming a crown core of a hardenable composite material on the tooth root and over the head portion of the inner post, the latter serving as an anchor for the crown core; and attaching an artificial crown over said crown core.

8. The method of claim 7, wherein said tooth is decoronated below the gingival margin.

9. A method of restoring a damaged or diseased tooth having a tooth root with a root canal, from which a tooth crown has been removed exposing said canal, comprising reaming out said canal with a reaming device;

cleaning said canal by acid-etching the reamed-out canal, irrigating the canal, and drying it;

applying a dentin bonding agent to the cleaned reamed canal;

loosely positioning in the reamed-out canal an outer post to form a space between said outer post and said canal, the outer post being formed of a perforated, open-ended generally cylindrical hollow body;

injecting a hardenable composite material into the canal through said outer post;

inserting into the outer post an inner post having a serrated post portion and a head portion at a proximal end of the post portion, the inserting including forcing said composite material through perforations in said hollow body outer post to fill the space between said canal and said outer post, said head portion being exposed above the tooth root;

forming a crown core of a hardenable composite material on the tooth root and over the head portion of the inner post, the latter serving as an anchor for the crown core; and attaching an artificial crown over said crown core.

10. An assembly for dental restoration of a damaged or diseased tooth having a tooth root with a root canal, from which a tooth crown has been removed exposing said canal and wherein the root canal has been suitably reamed and prepared for insertion of a dental post therein, the kit comprising at least one hollow, open-ended, generally cylindrical outer post body and suitably dimensioned to be loosely inserted into the prepared root canal of said tooth root;

at least one inner post having a serrated post portion at least slightly longer than said outer post body and loosely insertable within the latter, and a broadened head portion at a proximal end of the post portion; and at least one hollow core prep former dimensioned to overfit the head portion of said inner post on said root after the inner post has been inserted into the outer post body in the root canal of said tooth.

11. The assembly of claim 10, wherein there are a plurality of hollow outer post bodies of assorted lengths and a plurality of inner posts of assorted lengths.

12. The assembly of claim 11, wherein there are outer post bodies of substantially 9, 11, and 13 mm lengths, and there are inner posts of substantially 12, 14, and 16 mm lengths.

13. An assembly for dental restoration of a damaged or diseased tooth having a tooth root with a root canal, from which a tooth crown has been removed exposing said canal and wherein the root canal has been suitably reamed and prepared for insertion of a dental post assembly therein, the kit comprising at least one hollow, open-ended generally cylindrical outer post body of suitable dimension to be loosely inserted into the prepared root canal of said tooth root, and having a plurality of apertures along its length, the apertures increasing in size from an upper end to a lower end of the outer post body;

at least one inner post having a serrated post portion at least slightly longer than said outer post body and loosely insertable within the latter, and a head portion at an upper end of the post portion; and at least one hollow core prep former dimensioned to overfit the head portion of said inner post after the latter has been inserted into the outer post body in the root canal of said tooth.

14. The assembly of claim 13, wherein said at least one outer post body has a radial flange at its upper end.

15. An assembly for dental restoration of a damaged or diseased tooth having a tooth root with a root canal, from which a tooth crown has been removed exposing said canal and wherein the root canal has been suitably reamed and prepared for insertion of a dental post assembly therein, the kit comprising at least one hollow, open-ended, generally cylindrical outer post body capable of being cut to a suitable dimension to be loosely inserted into the prepared root canal of said tooth root;

at least one inner post having a serrated post portion at least slightly longer than said outer post body and loosely insertable into the latter, and a broadened, spade shaped head portion having a plurality of cut-outs therein to form a matrix for anchoring a composite core on which an artificial crown is to be affixed; and at least one core prep former dimensioned to overfit the head portion of said inner post on said root after the inner post has been inserted into the outer post body in the root canal of said tooth.

16. An assembly for dental restoration of a damaged or diseased tooth having a tooth root with a root canal, from which a tooth crown has been removed exposing said canal and wherein the root canal has been suitably reamed and prepared for insertion of a dental post assembly therein, the kit comprising at least one hollow, open-ended, generally cylindrical outer post body of suitable dimension to be loosely inserted into the prepared root canal of said tooth root;

at least one inner post having a serrated post portion at least slightly longer than said outer post body and insertable within the latter, and a broadened head portion, at least one inner post having a serrated post portion at least slightly longer than said outer post body and loosely insertable within said outer post body, and a head portion at a proximal end of the post portion;

a hollow crown prep former dimensioned to overfit the head portion of said inner post on said root after the inner post has been inserted into the outer post body in the root canal of said tooth;

suitable hardenable composite paste material to be injected through the outer post body into said root canal; and suitable hardenable composite material to be molded in the prep former to form a core, anchored by the head portion of said inner post, on which an artificial crown is to be secured.

17. A post assembly to be secured by means of a hardenable composite material to a cavity in a fixed member, comprising a hollow, open-ended generally cylindrical outer post body with apertures on a cylindrical wall thereof; and an inner post having a serrated post portion at least slightly longer than said outer body and loosely insertable in the latter and a broadened head portion at a proximal end of said inner post.

18. The post assembly of claim 17, wherein said apertures are progressively larger from a proximal to a distal end of the outer post body.

19. The post assembly of claim 17, wherein said head portion is spade shaped and has a plurality of cut-outs therein.

* * * * *